United States Patent [19]

Vilendrer

[11] Patent Number: 5,712,431

[45] Date of Patent: Jan. 27, 1998

[54] DEVICE AND METHOD FOR TESTING THE SHEAR RESPONSE OF A MATERIAL IN RESPONSE TO AN APPLIED FORCE

[75] Inventor: Kent Vilendrer, Eden Prairie, Minn.

[73] Assignee: Endura-Tec Systems Corporation, Eden Prairie, Minn.

[21] Appl. No.: 640,487

[22] Filed: May 1, 1996

[51] Int. Cl.$^6$ ........................................... G01N 3/24
[52] U.S. Cl. ........................... 73/841; 73/846; 73/853
[58] Field of Search ........................... 73/788, 818, 825, 73/841, 846, 849, 851, 852, 853

[56] References Cited

U.S. PATENT DOCUMENTS

| | | | |
|---|---|---|---|
| 3,035,437 | 5/1962 | Watkins et al. | 73/825 |
| 3,406,567 | 10/1968 | Terry | 73/101 |
| 3,566,681 | 3/1971 | Iosipescu et al. | 73/101 |
| 3,854,328 | 12/1974 | Schmidt | 73/803 |
| 3,975,950 | 8/1976 | Erdei | 73/825 |
| 4,445,387 | 5/1984 | Hall et al. | 73/845 |
| 4,854,175 | 8/1989 | Budhu | 73/841 |
| 4,916,954 | 4/1990 | Buzzard | 73/799 |
| 5,036,709 | 8/1991 | McRae | 73/841 |
| 5,245,876 | 9/1993 | Jones | 73/579 |
| 5,280,730 | 1/1994 | Peres et al. | 73/846 |
| 5,289,723 | 3/1994 | Thompson et al. | 73/842 |
| 5,461,928 | 10/1995 | Azzolini | 73/818 |

Primary Examiner—Richard Chilcot
Assistant Examiner—Max H. Noori
Attorney, Agent, or Firm—Haugen & Nikolai, PA

[57] ABSTRACT

A portable device for measuring the shear properties of compacted asphalt mixes under applied dynamic loading conditions. The device includes first and second material retaining members which form a material receiving pocket for containing the compacted asphalt mix. The first and second material retaining members are connected via flexure assemblies which allow movement of the first and second material retaining members only along the longitudinal axis of the compacted asphalt mix. A dynamic load is applied to the flexures, thereby creating a shear condition parallel to the longitudinal axis of the compacted mix. The temperature of the asphalt mix may be held constant by controlling the temperature within an environmental chamber through the use of a closed loop PID control system.

The specimen is dynamically loaded by a dynamic loading frame consisting of a servo pneumatic actuator and load reaction structure. A microprocessor-based controller operates the dynamic loading frame under closed loop control. The microprocessor-based controller may be servo controlled, utilizing feedback from either a load transducer or either of two linear displacement transducers.

16 Claims, 7 Drawing Sheets

DEVICE AND METHOD FOR TESTING THE SHEAR RESPONSE OF A MATERIAL IN RESPONSE TO AN APPLIED FORCE

BACKGROUND OF THE INVENTION

I. Field of the Invention

This invention relates generally to the field of asphalt characterization devices, and more particularly to a portable apparatus and method for testing the viscoelastic response of a material specimen to an applied shear force under either monotonic or dynamic loading conditions.

II. Discussion of the Related Art

Over the past several years, the Federal Highway Administration (FHWA) has been encouraging a modeling technique known as the SuperPave Asphalt Mix Design Model (hereinafter referred to as "superpave") as a method of predicting the life expectancy of various paving mixes. Paving mixes are typically custom tailored to the unique retirements dictated by local traffic, climate, materials selection, and structural section at the pavement site. The model is intended as a useful tool to help estimate the pavement's future long term performance in terms of it's resistance to permanent deformation (rutting), fatigue cracking and low temperature cracking.

The superpave modeling technique requires the input of mechanical properties associated with the particular asphalt mix to be modeled. In order to determine the required input properties of the asphalt mix, several tests are performed to determine the linear and non-linear elastic response, viscous behavior, and tertiary creep tendencies of the asphalt mix sample. These tests are characterized by the application of dynamic and monotonic loads or strains in shear and thereafter measuring the resulting strain or stress response. The resulting test data is then implemented in the superpave modeling technique to estimate the life expectancy of the sample.

In order to most effectively estimate the life expectancy of a sample using the superpave technique, the test data should be obtained at the field level. Hence, a portable testing apparatus is necessary to perform the required tests on the sample in the field. To further increase the efficiency of obtaining the required test data, the sample material should not require substantial specimen preparation.

Currently, the sample test data is obtained in a laboratory setting using cumbersome testing equipment known in art as a Superpave Shear Tester (hereinafter the "SST"). The SST includes a fixture that directs a shear load to a cylindrical specimen parallel with the ends of the specimen contained within the fixture. Proper use of the SST requires that the ends of a cylindrical specimen be cut square relative to each other and then glued to metal platens in a precision gluing jig prior to installation in the fixture. The "glued specimen" approach of the SST requires additional time and experience to properly glue and align the specimen. Further, in order to keep the ends of the specimen parallel, precise bearings are required to guide the specimen face as the shear load is applied. The use of bearings creates the possibility of backlash and misalignment. Hence, a need exists for a simple, portable device for testing the shear strength of a material in response to an applied force.

Various fixtures have been developed that direct a shear load to a specimen contained within the fixture. In this regard, reference is made to the disclosures of Iosipescu et al., U.S. Pat. No. 3,566,681, Jones, U.S. Pat. No. 5,245,876, Terry, U.S. Pat. No. 3,406,567, Hall et al. U.S. Pat. No. 4,445,387, Peres et al., U.S. Pat. No. 5,280,730, Thompson et al., U.S. Pat. No. 5,289,723, and Buzzard, U.S. Pat. No. 4,916,954 all describe fixtures for applying shear loads to a specimen. However, the disclosed fixtures do not apply a shear stress to the specimen wherein the applied force is both perpendicular to the outer cylindrical surface and along the longitudinal axis of the specimen. McRae in U.S. Pat. No. 5,036,709 discloses a method of compacting a specimen, prior to shear testing, the disclosure of which is incorporated herein by reference, however the compacting device is not simple and portable and further does not apply a force that is both perpendicular to the outer cylindrical surface and along the longitudinal axis of the specimen. Furthermore, the referenced devices do not disclose guides that inhibit twisting of the fixture as the shear load is applied. The present invention overcomes these and other disadvantages of the prior art.

SUMMARY OF THE INVENTION

The purpose of the present invention is to provide a portable field shear tester for determining shear stress test data corresponding to various asphalt mixes that can subsequently be used in modeling methods to estimate the future pavement life. Testing of the asphalt material is performed by compacting it into a cylindrical sample and placing it into a shear fixture that can be subjected to monotonic or dynamic forces. The shear fixture includes first and second material retaining members each having a concave arcuate surface. The arcuate surface of each retaining member is aligned diametrically opposite one another, thereby defining a material receiving pocket adapted for containing the cylindrical specimen. An applied force to the shear fixture, that is both perpendicular to the outer cylindrical surface and along the longitudinal axis of the specimen, causes a certain response in the cylindrical sample which can be measured from the displacement of the first and second material retaining members.

Those skilled in the art will appreciate that, although the preferred method of testing is to apply a load and thereafter measure the resulting displacement, an alternative test method would be to displace the sample a predetermined distance and then measure the load required to displace the sample the predetermined distance. To provide more control over the material properties, the specimen temperature is held constant by enclosing the shear fixture in an environmental control chamber.

Shear tests can be performed to stress levels of 2500KPA and strains to 5% at frequencies from 0 to 10 Hz. The device can perform various tests including a frequency sweep, simple shear and repeated shear to obtain relevant data corresponding to each test, the data of which is required in the superpave modeling technique. The applied load, specimen dimensions and measured displacement are then analyzed to determine the material stress/strain of the specimen associated with the required test data properties. These properties along with the controlled temperature are then used in the superpave modeling technique to thereby estimate the material's long term performance.

The shear tester generally includes a shear fixture with a displacement measuring transducer, loading frame with load transducer, an actuator with a displacement transducer, an environmental control chamber with temperature measurement transducer, and heating/cooling system. The shear fixture is coupled to a monitoring and control system which includes a microprocessor-based servocontroller, which controls, via closed loop feedback, the amplitude and frequency of the applied load or displacement to the shear fixture. A microprocessor-based temperature controller is also used to control the environmental chamber control temperature.

The shear fixture includes first and second material retaining members. Front and back restraint plates mounted to each retaining member prevent the specimen from expanding along it's longitudinal axis during the duration of the test. The back plates are bolted directly to the material retaining members. Without any limitation intended, the front plates are attached to the material retaining members via thumb screws. The thickness of the material retaining members is constant and the specimen lengths may vary from 50 to 150 mm. To accommodate the varied specimen lengths, specimen spacer plates are provided for shorter specimen lengths. The spacer lengths can be fabricated in different thicknesses as needed to accommodate any specimen length.

The two material retaining members are maintained in alignment with respect to one another by two flexures. The flexures allow movement of the retaining members in a direction that creates shearing of the specimen in a plane that is parallel to the specimen's longitudinal axis, while the specimen is maintained in a clamped position between the material retaining members.

Installation and removal of the specimen is facilitated by a threaded handle that temporarily increases the diameter of the cylindrical pocket. This creates a looser fit between the first and second material retaining members, thus allowing the specimen to be installed and removed easily.

The applied load or force to the fixture is measured by a load transducer that has one end coupled to an upper cross-piece of the shear fixture and the other end to a secondary flexure. The secondary flexure is attached to a shaft of the actuator. The secondary flexure or universal flexure accommodates small angular misalignments while transmitting the applied load to the shear fixture. A lower cross-piece and universal flexure is used to couple the lower cross-piece of the shear fixture to the cross-brace of the loading frame. A signal corresponding to the applied load is transmitted to a microprocessor-based controller which is coupled to the transducers for monitoring and control purposes and can be used to ensure that the test is being run at a specific load amplitude.

The relative movement of the first and second material retaining members is measured via a spring loaded displacement transducer which has it's body mounted to the second material retaining member and the measuring end pressed against the first material retaining member. A signal corresponding to the resulting displacement is transmitted to the microprocessor-based controller for monitoring and control purposes and can be used to ensure that the test is being run at a specific displacement amplitude. Those skilled in the art will appreciate that although a spring loaded LVDT type displacement transducer is preferred, other transducers used to measure the relative displacement of the first and second material retaining members could be used.

Both dynamic (sinusoidal or pulsed) or static loading can be applied to the shear fixture. A servo pneumatic actuator having a shaft coupled to the shear fixture is used to create the applied load. A servo valve mounted to the actuator ports high pressure supply air (typically 80–175 psi) to either side of an actuator piston. The resulting imbalance of air pressure creates the desired load or force in the desired direction. To energize the servo actuator separately from the air supply, an on/off solenoid valve is provided. The servo actuator is attached to the upper cross-brace of the loading frame and is attached via an actuator shaft to a cross-piece of the shear fixture. The lower part of the shear fixture attaches directly to a cross-brace of the loading frame. Those skilled in the art will appreciate that although a servo pneumatic actuator is used to generate the loading, other known load generators could be used including a servo hydraulic, electrodynamic or electromechanical generator.

The environmental control chamber surrounding the shear fixture is a box type configuration with a door for sealably enclosing the fixture and specimen. The chamber has both hot and cold capability and features an electric heater assembly and liquid $CO_2/N_2$ injector for cooling. Those skilled in the art will appreciate that other methods of heating/cooling could be used, however electric heat and liquid cooling are preferred. The chamber uses a temperature sensor for temperature readout and control. A signal corresponding to the resulting temperature is transmitted to the microprocessor-based temperature controller for monitoring and control purposes and can be used to ensure that the test is being run at a specific temperature.

OBJECTS

It is accordingly a principal object of the present invention to provide a shear tester for testing asphalt specimens at the field site for the purpose of generating test data that can be used in the superpave modeling technique.

Another object of the present invention is to provide a shear tester, wherein the specimen can be tested with minimal preparation at the field site.

Still another object of the present invention is to provide a means of shearing a cylindrical specimen along its longitudinal axis, wherein the shearing force is applied perpendicular to the cylindrical surface.

These and other objects, as well as these and other features and advantages of the present invention will become readily apparent to those skilled in the art from a review of the following detailed description of the preferred embodiment in conjunction with the accompanying drawings and claims, in which like numerals in the several views refer to corresponding parts.

DETAILED DESCRIPTION

Figure 1:
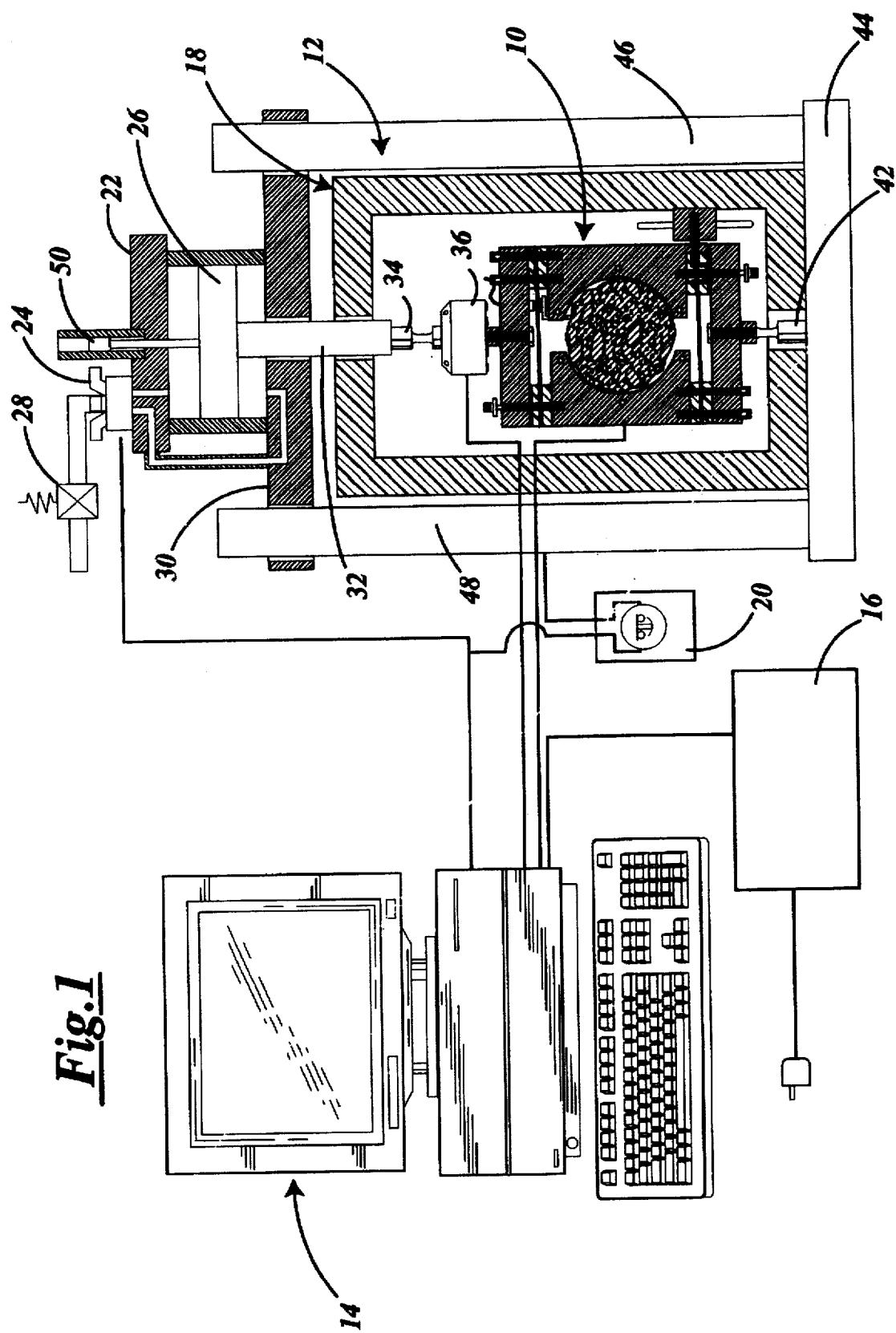
FIG. 1 is a partial block diagram view showing the complete field shear tester including the shear fixture, dynamic loading frame, environmental control chamber and microprocessor-based control system.

In conjunction with the several views of the figures, details of representative embodiments will next be presented. Referring first to FIG. 1, there is shown a shear fixture 10 connected to a frame 12, a microprocessor-based controller 14, an uninterruptable power supply 16, and an environmental control chamber 18. To provide a quick shutdown capability, a quick stop button 20 of suitable construction is electrically coupled to a solenoid valve 28.

Attached to the frame 12 is a servo pneumatic actuator 22 of known construction, with servo valve 24 for porting air to either side of the actuator piston 26. A solenoid valve 28 has on/off capability for manual control of the actuator 22, to thereby isolate the servo valve 24 from the air supply. In the preferred embodiment, the bottom 30 of the servo actuator 22 serves both as a bottom to the actuator 22 and a top cross-brace of the loading frame 12. One end of a shaft 32 is attached to the actuator piston 26, and the other end extends through the bottom 30 and is attached to a universal flexure 34.

The first end of a load transducer 36 is attached to the flexure 34 and the second end is attached to an upper cross-piece 38 of the shear fixture 10 (see FIGS. 1 and 3–7). A lower cross-piece 40 of the frame 12 is attached to a lower universal flexure 42 of known construction. The universal flexure 42 is further attached to a bottom cross-brace 44 of the frame 12. Two spaced vertical support columns 46, 48 are attached to and support the top and bottom cross-braces 30, 44.

Displacement transducer 50 is coupled to the actuator 22 and displacement transducer 52 is coupled to shear fixture 10. The transducers 50, 52 are of suitable known construction for measuring the respective displacement of the actuator 22 and fixture 10 and are electrically coupled to the microprocessor-based controller 14 to provide displacement feedback for closed loop servo control and monitoring.

Figure 2:
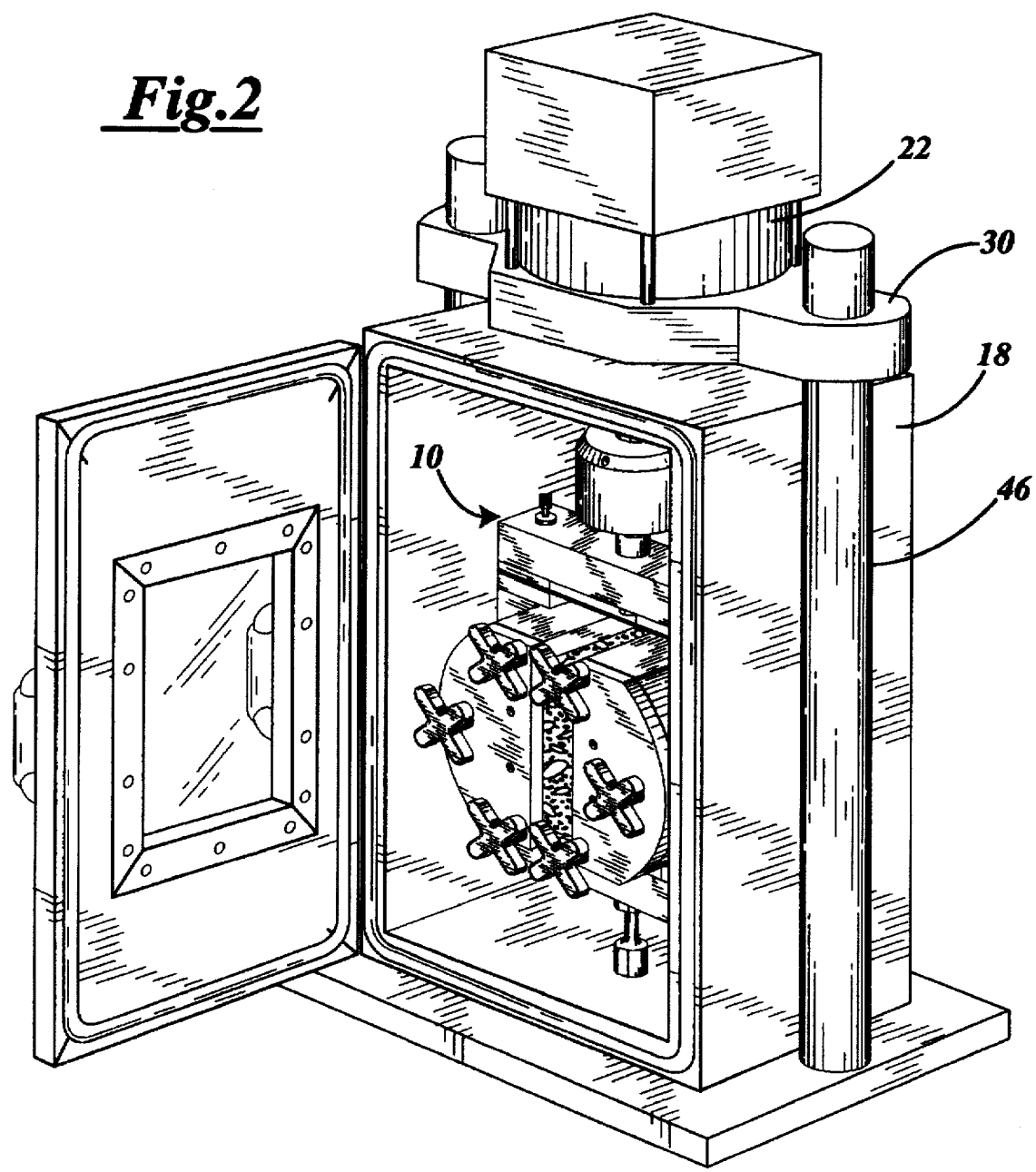
FIG. 2 is a front perspective view of the shear fixture installed in the environmental chamber and dynamic loading frame.
Figure 3:
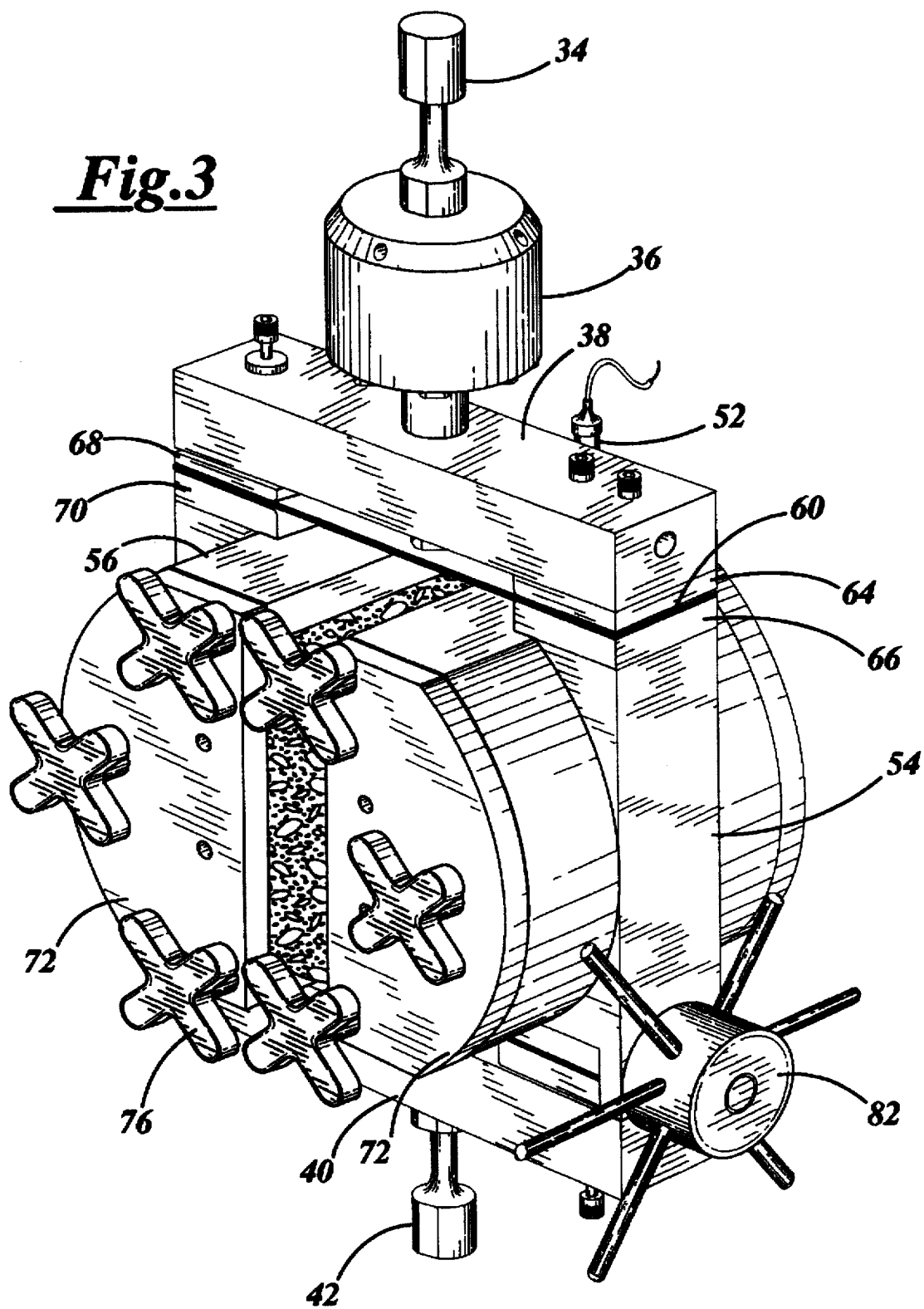
FIG. 3 is a front perspective view of the shear fixture showing an asphalt specimen installed for clarity.
Figure 4:
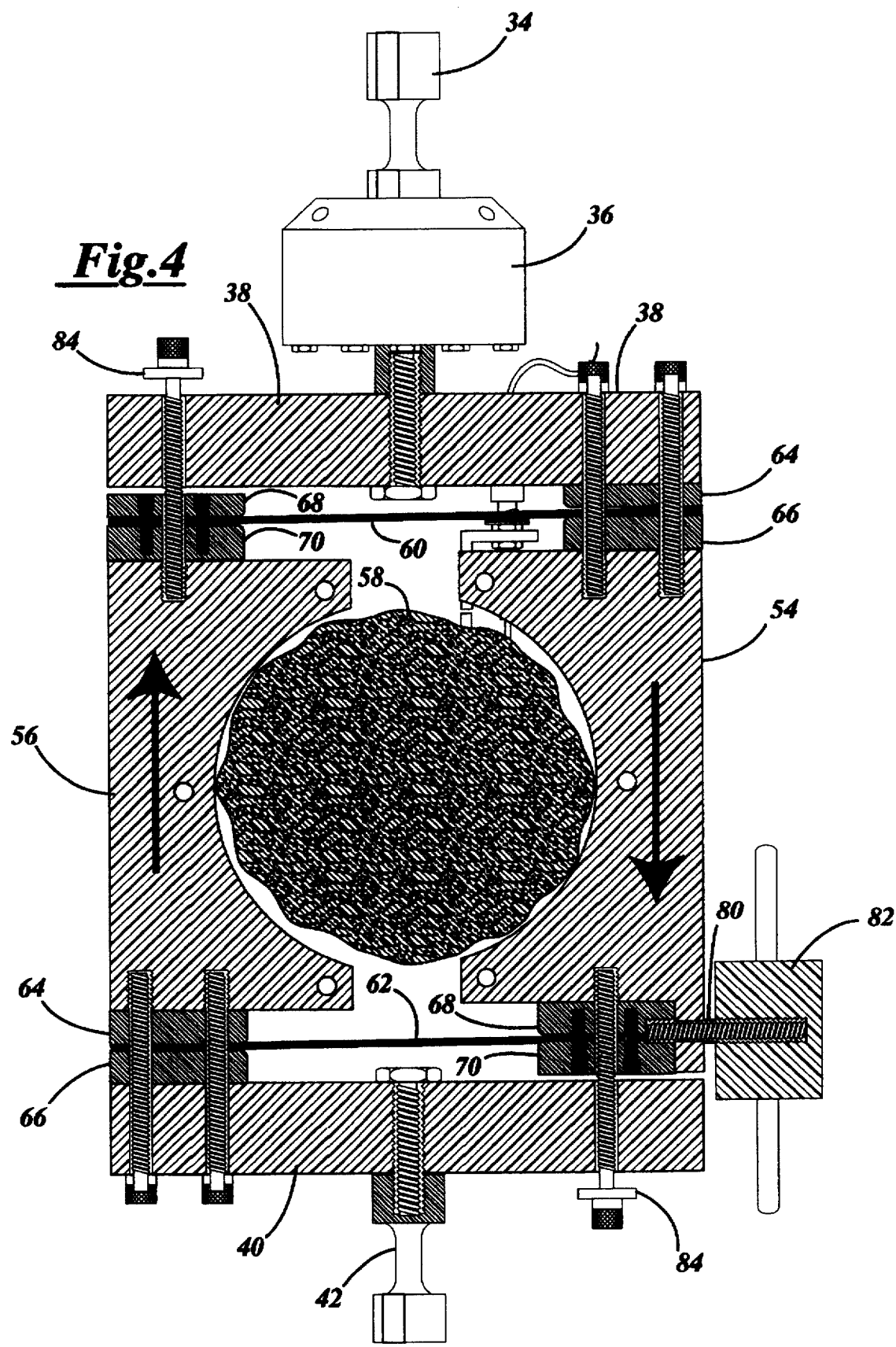
FIG. 4 is a front elevational view of the shear fixture of the type shown in FIG. 3 with the front restraint plates removed for clarity.
Figure 5:
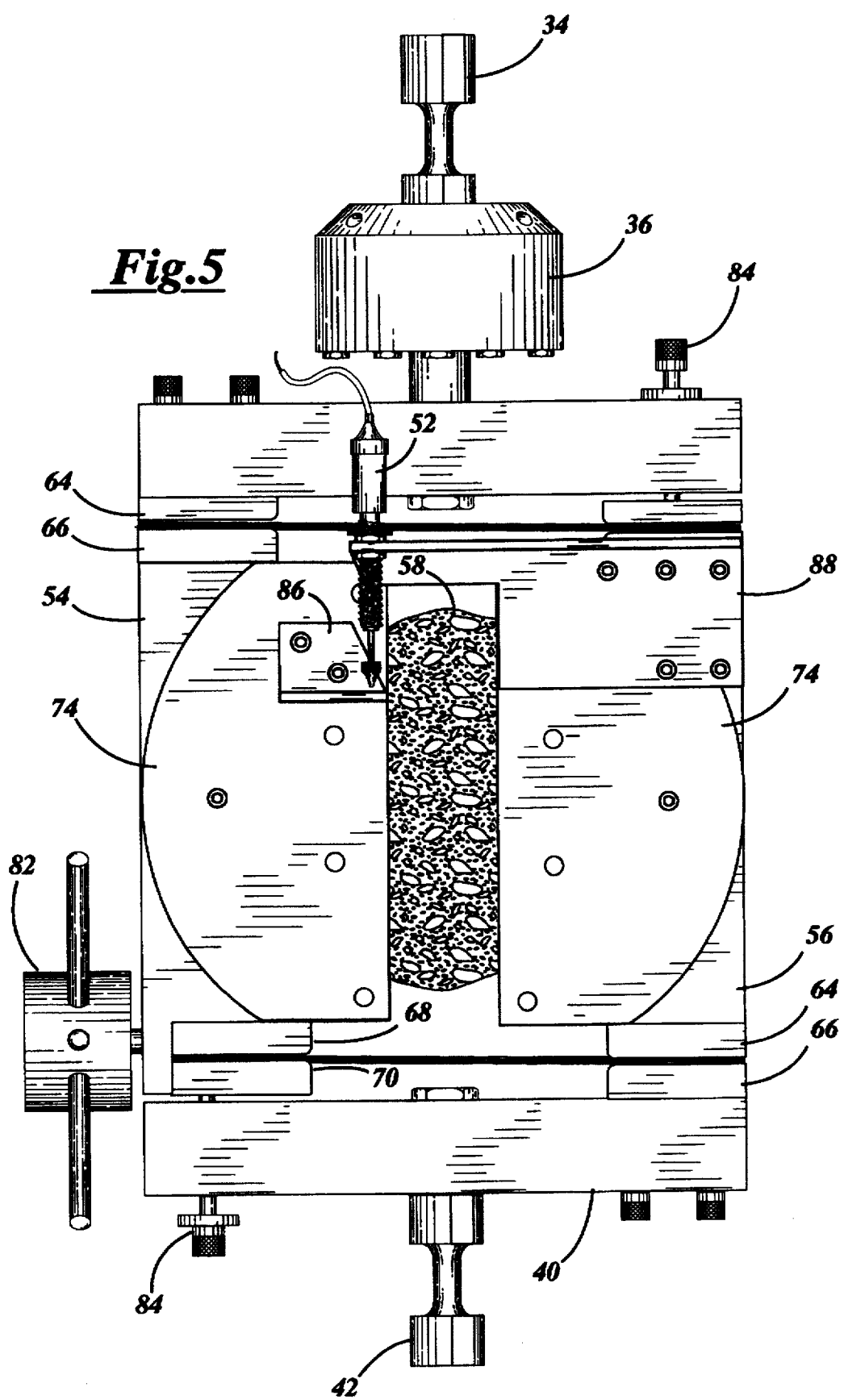
FIG. 5 is a back view of the shear fixture assembly.
Figure 6:
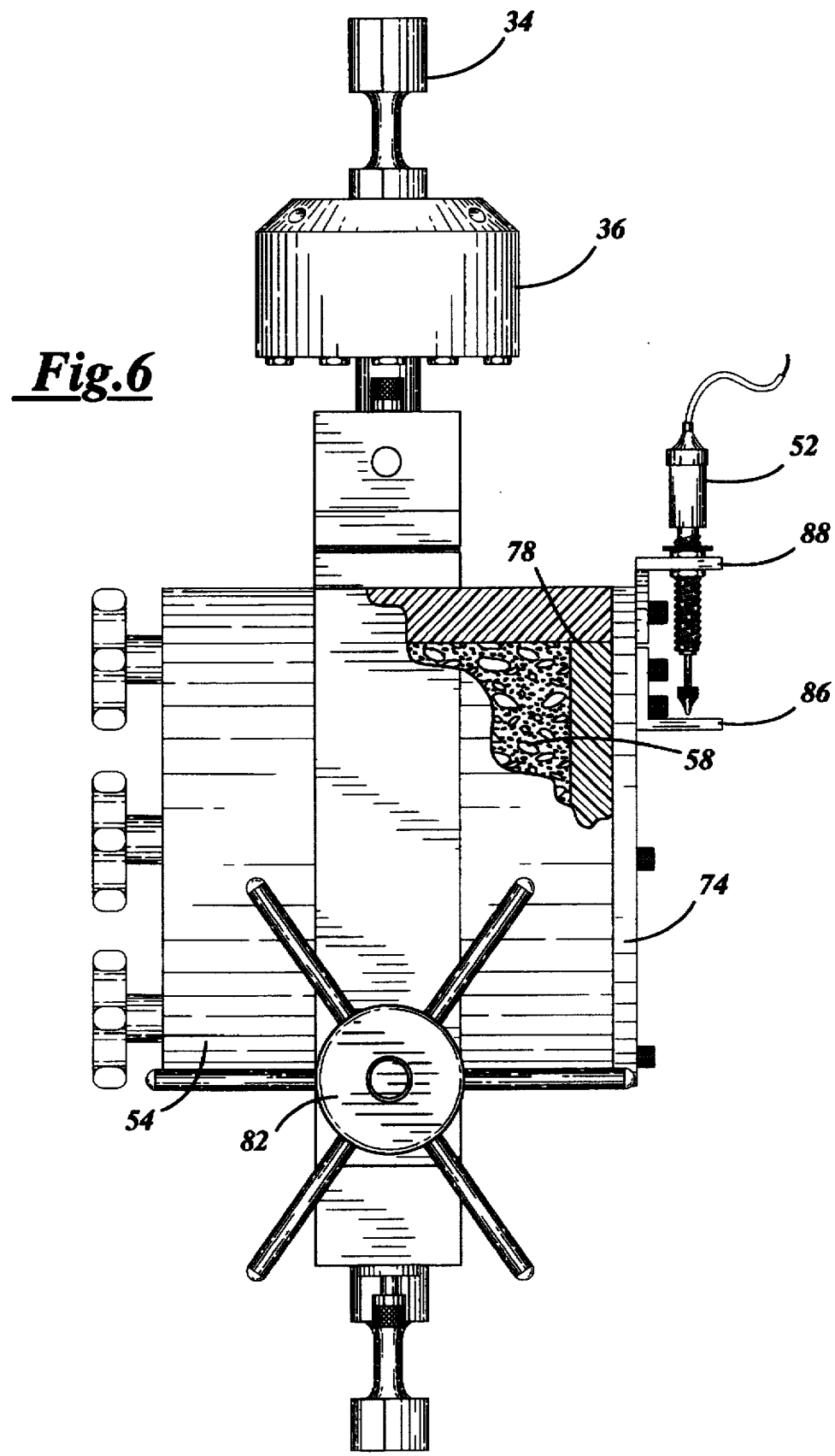
FIG. 6 is a partial elevational proximal view of the shear fixture assembly.
Figure 7:
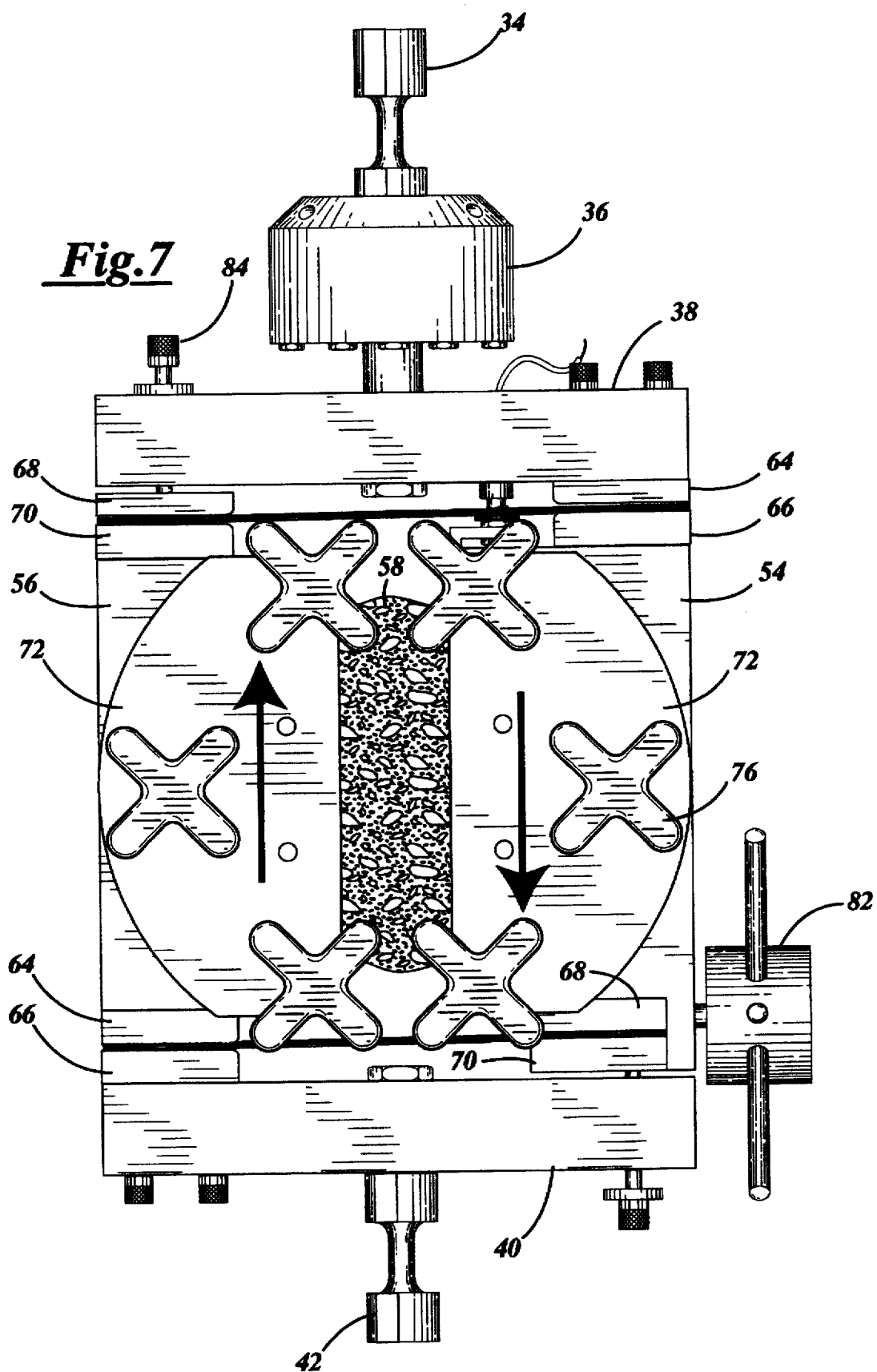
FIG. 7 is a front view of the shear fixture assembly showing the applied force and resulting displacement directions.

In order to reduce the influence of temperature variances on the resulting test data, the shear fixture 10 is placed within an environmental control chamber 18 which surrounds the fixture 10 (see FIGS. 1 and 2). The environmental chamber 18 has hot/cold capability to maintain the temperature at a fixed level throughout the test. The environmental chamber 18 maintains the specimen temperature at a predetermined setting and is capable of either increasing or decreasing the temperature within the chamber 18. In this regard, the chamber has a temperature transducer, an electric heater assembly for heating and a liquid $CO_2/N_2$ injector for cooling. The temperature transducer and heating/cooling elements within the chamber 18 are coupled to a microprocessor-based temperature controller (not shown). A signal is sent from the temperature transducer to the temperature controller, indicating the temperature of the chamber air temperature. When the temperature controller determines that the inside air temperature is below a preset level, the heating elements are activated until the inside air temperature rises to the desired temperature. When the temperature controller determines that the inside air temperature is above the preset level, a solenoid valve is opened thereby cycling $CO_2/N_2$ until the air temperature drops to the desired temperature.

The microprocessor-based temperature controller uses a PID control algorithm, whereby the temperature transducer signal is compared to a desired setpoint value. The difference or "error" is then scaled using a proportional (P) calculation, integrated over time and scaled using an Integration (I) calculation and differentiated with respect to time and scaled using a Differentiation (D) calculation. The temperature P, I, and D values are then summed together and the resulting value is used to drive a solid state relay using a Pulse Width Modulation (PWM) technique. The solid state relay activates the heating elements or injection solenoids, when necessary, to maintain the fluid temperature at the desired temperature setpoint.

Referring now to FIGS. 3–7, the shear fixture 10 is comprised generally of upper and lower cross-pieces 38, 40, upper and lower flexure assemblies (which include flexures 60, 62 and spacers 64–70), first and second material retaining members 54, 56, each having a concave arcuate surface aligned diametrically opposite one another to form a cylindrical pocket to accommodate the material specimen 58, and restraint plates 72, 74. Alignment of the first and second material retaining members 54, 56 is accomplished using upper and lower flexure assemblies. A proximal end of the upper flexure 60 is attached between the proximal end of the upper cross-piece 38 and the first material retaining member 54. An upper spacer 64 separates the upper cross-piece 38 and upper flexure 60. Attached to the distal end of the flexure 60 are spacer members 68 and 70 having a combined thickness that is less than the combined thickness of spacers 64 and 66. The lower flexure 62 is attached between the lower cross-piece 40 and second material retaining member 56 in a similar manner wherein the distal end of the lower flexure 62 is fixedly attached between the lower cross-piece 40 and second material retaining member 56. The upper and lower flexures 60 and 62 allow movement of the material retaining members 54, 56 in the vertical direction creating a shear condition along the specimen's longitudinal axis, while at the same time the flexures 60, 62 maintain the specimen in fixed position between the material retaining members 54, 56.

Front and back restraint plates 72, 74 are attached to each material retaining members 54, 56, thereby inhibiting the specimen 58 from expanding along it's longitudinal axis during the test. The back plates 74 are bolted directly to the material retaining members 54, 56 while the front plates 72 are attached to the material retaining members 54, 56 via thumb screws 76. Those skilled in the art will appreciate that other methods of attachment could be used. Although the thickness of the material retaining members 54, 56 is fixed and the specimen lengths may vary from 50 to 150 mm. To accommodate for various specimen lengths, spacer plates 78 are provided for shorter specimens.

Installation and removal of the specimen is facilitated by a stud 80 and threaded handle assembly 82 that couples the proximal end of the lower flexure 62 to the bottom of the first material retaining member 54. Tightening the stud 80 and handle 82 against the first material retaining member 54 increases the distance between the lower portion of the material retaining members 54, 56. This creates a looser fit between the material retaining members 54, 56, thus allowing specimen 58 to be installed and removed easily.

As described above the upper cross-piece 38 is attached to the load transducer 36 and the lower cross-piece is attached to universal flexure 42. To reduce excessive over travel and damage to the flexure assemblies in the event of a specimen failure, shoulder bolts or over travel stops 84 are used. Likewise, spacers 68, 70 inhibit over travel in the event a compression failure. The shoulder bolts 84 and spacers 68, 70 ensures that the material retaining members 54, 56 can only move a small distance with respect to one another. Universal flexures 34 and 42 also reduce extraneous side loads and moments from being transmitted to the load transducer 36 and fixture 10.

As an upward or downward force is applied by the actuator 22, the load transducer may stretch or compress slightly. For this reason, the actuator displacement transducer 50 cannot be used as a reliable indication of relative displacement between the material retaining members 54, 56. The material retaining members 54, 56 relative displacement is measured via a spring loaded displacement transducer 52 which has it's body mounted to the second material retaining member 56 via bracket 88 and the measuring end of the transducer 52 is pressed against bracket 86 attached to the first material retaining member 54. A signal corresponding to the measured displacement is transmitted to the microprocessor-based controller 14 for monitoring and control purposes and can be used to ensure that the test is being run at a specific displacement amplitude.

The microprocessor-based controller 14 uses a PID control algorithm for controlling the servo pneumatic actuator 22. The feedback signals from either the load transducer 36 or linear displacement transducers 50 and 52 are amplified and then converted to a digital value by means of an internal analog to digital converter. Over time the resulting digitized feedback value can be represented as a waveform. This waveform is then subtracted from a baseline or desired "command waveform". The resulting waveform or "error signal" is typically sinusoidal with respect to time if the "command waveform" is sinusoidal. Although the control of the servo pneumatic actuator feedback signal may correspond to a load or pressure within the actuator, load control is presently preferred, wherein the displacement feedback is used to monitor the specimen response.

After the error signal is computed, the microprocessor 14 then performs several mathematical operations on the error signal known as PID control. First, the error signal is multiplied by a scaler value $K_1$ to obtain a proportional (P) value. The error signal is also integrated over time and multiplied by scaler value $K_2$ to obtain an Integration (I) value. The error value is also differentiated with respect to time and multiplied by scaler value $K_3$ to obtain a differentiation (D) value. The P, I, and D values are then summed together and converted to a proportional drive output voltage by means of a digital to analog converter built into the microprocessor-based controller 14. This output voltage is the input signal for the servo valve 24 which controls the force applied by the actuator. The PID control tends to reposition the applied load of the servo pneumatic actuator 22 to minimize the error signal.

To further enhance the accuracy of the control loop and maintain the desired applied load, the peak end levels of the feedback signal from load transducer 36 is monitored by the microprocessor based controller 14. If the peak end levels of the feedback signal vary from a predetermined peak level (ie: due to changing specimen compliance conditions, changes in supply pressure, etc.), the software automatically adjusts the command waveform used in the PID control until the desired feedback signal end level is achieved.

Having described the constructional features of the present invention, the mode of use will now be discussed. The user loosens threaded handle 82 of the shear fixture 10 so that the material retaining members 54, 56 move apart. The user then positions servo actuator 22 via microprocessor-based controller 14 until cylindrical specimen 58 fits between the two saddles. After inserting the specimen 58 until it is flush against back restraining plates 74, the user turns threaded handle 82 until the material retaining members 54 is tight against the lower flexure 62. The operator then attaches front restraining plates 72, tightening the plate 72 against the specimen 58 using hand screws 76. With the specimen installed, the user selects the desired applied load profile using the microprocessor-based controller. As the desired load (frequency sweep, simple shear, and repeated shear) is applied, the microprocessor based controller 14 measures the applied load and resulting displacement as a function of time. Depending on the material characteristic to be determined, the microprocessor program performs the required analysis and data storage. Upon completion of the test, the user removes front retraining plates 72 and extracts the specimen 58 from the shear fixture 10.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A device used for testing a response of a cylindrical specimen to shear forces applied to the cylindrical specimen, said device comprising:

(a) upper and lower spaced cross-pieces;

(b) upper and lower spaced flexure assemblies each having a proximal and distal end, said proximal end of said upper flexure assembly being attached to a corresponding proximal end of the upper cross-piece and said distal end of said lower flexure assembly being attached to a corresponding distal end of the lower cross-piece; and (c) first and second specimen retaining members each including a concave arcuate surface, said first specimen retaining member aligned between the proximal end of said upper and lower flexure assemblies and said second specimen retaining member aligned between the distal end of said upper and lower flexure assemblies, said first retaining member being attached to the proximal end of said upper flexure assembly and coupled to the proximal end of the lower flexure assembly, said second retaining member being attached to the distal end of said lower flexure assembly and coupled to the distal end of the upper flexure assembly, wherein the arcuate surface of each said first and second retaining members are aligned diametrically opposite one another, thereby defining a material receiving pocket adapted for containing the cylindrical specimen, whereby a downward force to the upper cross-piece causes the proximal end of the upper flexure assembly and the first retaining member to move downward and the distal end of the lower flexure assembly and the second retaining member to move upward while the upper and lower flexure assemblies maintain a relative distance and alignment between the first and second retaining members.

2. The device as recited in claim 1, further including a first overtravel stop attached to the second retaining member and integral with the distal end of said upper cross-plate, and a second overtravel stop attached to the first retaining member and integral with the proximal end of said lower cross-plate to inhibit overloading of the upper and lower flexure assemblies.

3. The device as recited in claim 1, further comprising a linear displacement transducer coupled between the first and second retaining members to thereby measure the relative displacement between the first and second retaining members.

4. The device as recited in claim 1, further comprising a first restraint plate attached to a front side of the first and second retaining members and a second restraint plate attached to a back side of the first and second retaining members.

5. The device as recited in claim 1, further including means integral with said device for controlling a temperature of the cylindrical specimen.

6. The device as recited in claim 3, further comprising a frame and an actuator attached to said frame, said actuator including a shaft attached to said upper cross-piece wherein a force is applied from the actuator through the shaft to said upper cross-piece.

7. The device as recited in claim 6, further comprising a control means for adjusting the forge applied by the actuator to said upper cross-piece, and for monitoring a resulting displacement of the first and second material retaining members, said control means being electrically coupled to said linear transducer and said actuator.

8. The device as recited in claim 7, further comprising an uninterruptable power supply electrically coupled to said control means.

9. The device as recited in claim 7, further comprising a load transducer attached to the shaft of said actuator and electrically coupled to the control means.

10. An apparatus for testing a response of a cylindrical specimen to shear forces applied to a longitudinal axis of the cylindrical specimen, said apparatus comprising:

(a) a frame having a spaced top and bottom cross-brace and a vertical column having a first end attached to the top cross-brace and a second end attached to the bottom cross-brace;

(b) an actuator attached to the top cross-brace of said frame, said actuator including a shaft extending downward therefrom, said shaft being operably displaced between a first extended position and a second retracted position;

(c) an upper cross-piece attached to a free end of said shaft of said actuator;

(d) a lower cross-piece attached to said bottom cross-brace;

(e) upper and lower spaced flexure assemblies each having a proximal and distal end, said proximal end of said upper flexure assembly being attached to a corresponding proximal end of the upper cross-piece and said distal end of said lower flexure assembly being attached to a corresponding distal end of the lower cross-piece; and (f) first and second spaced material retaining members each including a concave arcuate surface, said first specimen retaining member aligned between the proximal end of said upper and lower flexure assemblies and said second specimen retaining member aligned between the distal end of said upper and lower flexure assemblies, said first retaining member being attached to the proximal end of said upper flexure assembly and coupled to the proximal end of said lower flexure assembly said second retaining member being attached to the distal end of said lower flexure assembly and coupled to the distal end of said upper flexure assembly, wherein the arcuate surface of each said first and second retaining members are aligned diametrically opposite one another, thereby defining a material receiving pocket adapted for containing the cylindrical specimen, whereby a downward force to the upper cross-piece from the displacement of the shaft causes the proximal end of the upper flexure assembly and the first retaining member to move downward and the distal end of the lower flexure assembly and the second retaining member to move upward while the upper and lower flexure assemblies maintain a relative distance and alignment between the first and second retaining members.

11. The apparatus as recited in claim 10, further including a first over travel stop attached to the second retaining member and integral with the distal end of said upper cross-plate, and a second over travel stop attached to the first retaining member and integral with the proximal end of said lower cross-plate to inhibit overloading of the upper and lower flexure assemblies.

12. The apparatus as recited in claim 10, further comprising a linear displacement transducer coupled between the first and second retaining members to thereby measure the relative displacement between the first and second retaining members.

13. The apparatus as recited in claim 10, further comprising a first restraint plate attached to a front side of the first and second retaining members and a second restraint plate attached to a back side of the first and second retaining members.

14. The apparatus as recited in claim 10, further including means integral with said device for controlling a temperature of the cylindrical specimen.

15. The apparatus as recited in claim 10, further comprising a control means for adjusting a force applied by the actuator to said upper cross-piece, and for monitoring a resulting displacement of the first and second material retaining members, said control means being electrically coupled to said linear transducer and said actuator.

16. The apparatus as recited in claim 15, further comprising a load transducer attached to the shaft of said actuator and electrically coupled to the control means.

* * * * *